(12) United States Patent
Althaus et al.

(10) Patent No.: US 12,038,397 B2
(45) Date of Patent: Jul. 16, 2024

(54) DETERMINING ROCK SAMPLE PROPERTIES

(71) Applicant: Saudi Arabian Oil Company, Dhahran (SA)

(72) Inventors: Stacey M. Althaus, Katy, TX (US); Jin-Hong Chen, Houston, TX (US)

(73) Assignee: Saudi Arabian Oil Company, Dhahran (SA)

( * ) Notice: Subject to any disclaimer, the term of this patent is extended or adjusted under 35 U.S.C. 154(b) by 198 days.

(21) Appl. No.: 17/854,391

(22) Filed: Jun. 30, 2022

(65) Prior Publication Data
US 2024/0003838 A1   Jan. 4, 2024

(51) Int. Cl.
  *G01N 24/08*   (2006.01)
  *G01N 33/24*   (2006.01)

(52) U.S. Cl.
  CPC ......... *G01N 24/081* (2013.01); *G01N 33/241* (2013.01)

(58) Field of Classification Search
  CPC ............................. G01N 24/081; G01N 33/241
  See application file for complete search history.

(56) References Cited

U.S. PATENT DOCUMENTS

| | | | | |
|---|---|---|---|---|
| 8,230,918 B2* | 7/2012 | Ameen | ................. | E21B 47/11 166/250.1 |
| 10,436,727 B2* | 10/2019 | Valori | ................. | G01N 24/081 |
| 2020/0166449 A1* | 5/2020 | Green | ................. | G01R 33/30 |
| 2020/0363352 A1 | 11/2020 | King et al. | | |

OTHER PUBLICATIONS

Sing et al., "Reporting Physisorption Data for Gas/Solid Systems with Special Reference to the Determination of Surface Area and Porosity," Pure & Applied Chemistry, 57(4), 1985, 603-619, 17 pages.

Thommes et al., "Physisorption of gases, with special reference to the evaluation of surface area and pore size distribution (IUPAC Technical Report)," Pure and Applied Chemistry, 87(9-10), Jul. 2015, 1051-1069, 19 pages.

Veselinovic et al., "Measurement of Natural Gas Isotherms and Imaging Gas in Shale Using NMR," Unconventional Resources Technology Conference, Jul. 2018, 8 pages.

Wang et al., "A review of common practices in gravimetric and volumetric adsorption kinetic experiments," Adsorption, 27, Nov. 2020, 295-318, 24 pages.

\* cited by examiner

*Primary Examiner* — Gregory H Curran
(74) *Attorney, Agent, or Firm* — Fish & Richardson P.C.

(57) ABSTRACT

Techniques for determining at least one rock property of a core sample include measuring a first nuclear magnetic resonance (NMR) spectrum signal of a test fluid enclosed at a particular pressure in a cylinder of an NMR pressure cell; measuring a second NMR spectrum signal of a core sample immersed in the test fluid; removing a background NMR spectrum signal from the first and second NMR spectrum signals to determine a bulk test fluid NMR spectrum signal and a combined test fluid and core sample NMR spectrum signal; determining a porosity of the core sample based on the bulk test fluid NMR spectrum signal, the combined test fluid and core sample NMR spectrum signal, a dimension of the core sample, and a dimension of the cylinder; and determining a fluid intake capacity of the core sample based on the porosity and the dimension of the core sample.

26 Claims, 9 Drawing Sheets

DETERMINING ROCK SAMPLE PROPERTIES

TECHNICAL FIELD

The present disclosure describes systems and methods for determining properties of a rock sample.

BACKGROUND

An amount of fluid that is able to be injected into a porous rock sample gives information on the pore space and fluid storage capacity of the rock sample. Conventional measurement methods largely include two types of measurements: volumetric methods and gravimetric methods. Most of these methods use a small amount of the rock sample in powder form, and the change in volume/weight is then monitored as an indirect method to measure fluid uptake. The configuration and maintenance of these systems are crucial for valid measurement, however, many conventional systems do not undergo a rigorous testing needed.

SUMMARY

In an example implementation, a method for determining at least one rock property of a core sample includes measuring a first nuclear magnetic resonance (NMR) spectrum signal of a test fluid enclosed at a particular pressure in a cylinder of an NMR pressure cell; measuring a second NMR spectrum signal of a core sample immersed in the test fluid that is enclosed at the particular pressure in the cylinder of the NMR pressure cell; removing a background NMR spectrum signal from the first and second NMR spectrum signals to determine a bulk test fluid NMR spectrum signal and a combined test fluid and core sample NMR spectrum signal; determining a porosity of the core sample based on the bulk test fluid NMR spectrum signal, the combined test fluid and core sample NMR spectrum signal, at least one dimension of the core sample, and at least one dimension of the cylinder; and determining a fluid intake capacity of the core sample based at least in part on the porosity and the at least one dimension of the core sample.

In an aspect combinable with the example implementation, removing the background NMR spectrum signal from the first and second NMR spectrum signals includes removing a first background NMR spectrum signal from the first NMR spectrum signal; and removing a second background NMR spectrum signal from the second NMR spectrum signal.

Another aspect combinable with any of the previous aspects further includes measuring the first background NMR spectrum signal of the cylinder at a vacuum and independent of the test fluid and the rock sample; and measuring the second background NMR spectrum signal of the cylinder with the rock sample at a vacuum and independent of the test fluid.

In another aspect combinable with any of the previous aspects, removing the first background NMR spectrum signal from the first NMR spectrum signal includes subtracting an amplitude of the first background NMR spectrum signal from an amplitude of the first NMR spectrum signal across a chemical shift.

In another aspect combinable with any of the previous aspects, removing the second background NMR spectrum signal from the second NMR spectrum signal includes subtracting an amplitude of the second background NMR spectrum signal from an amplitude of the second NMR spectrum signal across the chemical shift.

In another aspect combinable with any of the previous aspects, the at least one dimension of the core sample includes a cross-sectional radius or diameter of the core sample, and the at least one dimension of the cylinder includes a cross-sectional radius or diameter of an inner volume of the cylinder.

In another aspect combinable with any of the previous aspects, determining the fluid intake capacity of the core sample based at least in part on the porosity and the at least one dimension of the core sample includes determining the fluid intake capacity of the core sample based on the porosity, the cross-sectional radius or diameter of the core sample, and a length of the core sample.

In another aspect combinable with any of the previous aspects, the core sample is cylindrical.

In another aspect combinable with any of the previous aspects, the test fluid includes methane, and the NMR spectrum signal includes a $^1H$ or a $^{13}C$ signal.

In another aspect combinable with any of the previous aspects, the test fluid includes carbon dioxide, and the NMR spectrum signal includes a $^{13}C$ signal.

In another example implementation, a system for determining at least one rock property of a core sample includes a nuclear magnetic resonance (NMR) pressure cell and a control system. The NMR pressure cell includes a test cylinder configured to hold a test fluid and a core sample; and an NMR coil positioned around the test cylinder and configured to measure NMR spectrum signals of the test cylinder. The control system is communicably coupled to the NMR coil and configured to perform operations including measuring a first nuclear magnetic resonance (NMR) spectrum signal of the test fluid enclosed at a particular pressure in the test cylinder; measuring a second NMR spectrum signal of the core sample immersed in the test fluid that is enclosed at the particular pressure in the test cylinder; removing a background NMR spectrum signal from the first and second NMR spectrum signals to determine a bulk test fluid NMR spectrum signal and a combined test fluid and core sample NMR spectrum signal; determining a porosity of the core sample based on the bulk test fluid NMR spectrum signal, the combined test fluid and core sample NMR spectrum signal, at least one dimension of the core sample, and at least one dimension of the test cylinder; and determining a fluid intake capacity of the core sample based at least in part on the porosity and the at least one dimension of the core sample.

In an aspect combinable with the example implementation, the operation of removing the background NMR spectrum signal from the first and second NMR spectrum signals includes removing a first background NMR spectrum signal from the first NMR spectrum signal; and removing a second background NMR spectrum signal from the second NMR spectrum signal.

In another aspect combinable with any of the previous aspects, the control system is configured to perform operations including measuring the first background NMR spectrum signal of the cylinder at a vacuum and independent of the test fluid and the rock sample; and measuring the second background NMR spectrum signal of the cylinder with the rock sample at a vacuum and independent of the test fluid.

In another aspect combinable with any of the previous aspects, the operation of removing the first background NMR spectrum signal from the first NMR spectrum signal includes subtracting an amplitude of the first background NMR spectrum signal from an amplitude of the first NMR spectrum signal across a chemical shift.

In another aspect combinable with any of the previous aspects, the operation of removing the second background NMR spectrum signal from the second NMR spectrum signal includes subtracting an amplitude of the second background NMR spectrum signal from an amplitude of the second NMR spectrum signal across the chemical shift.

In another aspect combinable with any of the previous aspects, the at least one dimension of the core sample includes a cross-sectional radius or diameter of the core sample, and the at least one dimension of the cylinder includes a cross-sectional radius or diameter of an inner volume of the cylinder.

In another aspect combinable with any of the previous aspects, the operation of determining the fluid intake capacity of the core sample based at least in part on the porosity and the at least one dimension of the core sample includes determining the fluid intake capacity of the core sample based on the porosity, the cross-sectional radius or diameter of the core sample, and a length of the core sample.

In another aspect combinable with any of the previous aspects, the core sample is cylindrical.

In another aspect combinable with any of the previous aspects, the test fluid includes methane, and the NMR spectrum signal includes a $^1$H or a $^{13}$C signal.

In another aspect combinable with any of the previous aspects, the test fluid includes carbon dioxide, and the NMR spectrum signal includes a $^{13}$C signal.

In another example implementation, a computer-implemented method for determining at least one rock property of a core sample includes identifying, with at least one hardware processor, measurements of a first nuclear magnetic resonance (NMR) spectrum signal of a test fluid enclosed at a particular pressure in a cylinder of an NMR pressure cell; identifying, with the at least one hardware processor, measurements of a second NMR spectrum signal of a core sample immersed in the test fluid that is enclosed at the particular pressure in the cylinder of the NMR pressure cell; removing, with the at least one hardware processor, a background NMR spectrum signal from the first and second NMR spectrum signals to determine a bulk test fluid NMR spectrum signal and a combined test fluid and core sample NMR spectrum signal; determining, with the at least one hardware processor, a porosity of the core sample based on the bulk test fluid NMR spectrum signal, the combined test fluid and core sample NMR spectrum signal, at least one dimension of the core sample, and at least one dimension of the cylinder; and determining, with the at least one hardware processor, a fluid intake capacity of the core sample based at least in part on the porosity and the at least one dimension of the core sample.

In an aspect combinable with the example implementation, removing the background NMR spectrum signal from the first and second NMR spectrum signals includes removing, with the at least one hardware processor, a first background NMR spectrum signal from the first NMR spectrum signal; and removing, with the at least one hardware processor, a second background NMR spectrum signal from the second NMR spectrum signal.

Another aspect combinable with any of the previous aspects further includes identifying, with the at least one hardware processor, measurements of the first background NMR spectrum signal of the cylinder at a vacuum and independent of the test fluid and the rock sample; and identifying, with the at least one hardware processor, measurements of the second background NMR spectrum signal of the cylinder with the rock sample at a vacuum and independent of the test fluid.

In another aspect combinable with any of the previous aspects, removing the first background NMR spectrum signal from the first NMR spectrum signal includes subtracting, with the at least one hardware processor, an amplitude of the first background NMR spectrum signal from an amplitude of the first NMR spectrum signal across a chemical shift.

In another aspect combinable with any of the previous aspects, removing the second background NMR spectrum signal from the second NMR spectrum signal includes subtracting, with the at least one hardware processor, an amplitude of the second background NMR spectrum signal from an amplitude of the second NMR spectrum signal across the chemical shift.

In another aspect combinable with any of the previous aspects, the at least one dimension of the core sample includes a cross-sectional radius or diameter of the core sample, and the at least one dimension of the cylinder includes a cross-sectional radius or diameter of an inner volume of the cylinder.

In another aspect combinable with any of the previous aspects, determining the fluid intake capacity of the core sample based at least in part on the porosity and the at least one dimension of the core sample includes determining, with the at least one hardware processor, the fluid intake capacity of the core sample based on the porosity, the cross-sectional radius or diameter of the core sample, and a length of the core sample.

In another aspect combinable with any of the previous aspects, the test fluid includes methane, and the NMR spectrum signal includes a $^1$H or a $^{13}$C signal.

In another aspect combinable with any of the previous aspects, the test fluid includes carbon dioxide, and the NMR spectrum signal includes a $^{13}$C signal.

Implementations of systems and methods for determining core sample properties according to the present disclosure can include one, some, or all of the following features. For example, systems and methods for determining core sample properties according to the present disclosure can utilize nuclear magnetic resonance (NMR) measurements on whole rock samples to determine a fluid intake capacity of the rock sample. As another example, systems and methods for determining core sample properties according to the present disclosure can utilize a single rock sample in multiple NMR test procedures with multiple test fluids. As another example, systems and methods for determining core sample properties according to the present disclosure can provide for direct methods of measuring a fluid uptake in a rock sample, including carbon dioxide or hydrocarbons.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

Figure 1B:
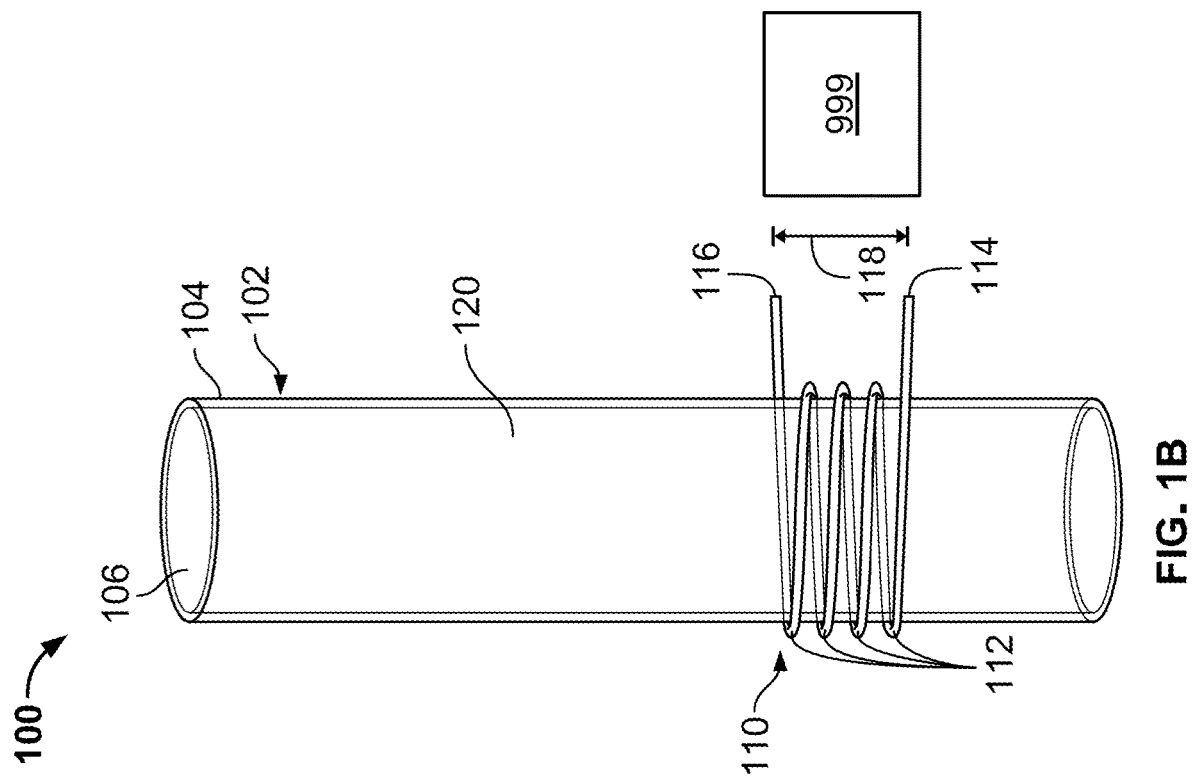
FIGS. 1A-1D are schematic drawings of a rock property measurement system as used in sequential steps in an example method for determining one or more properties of a rock core sample according to the present disclosure.
Figure 1A:
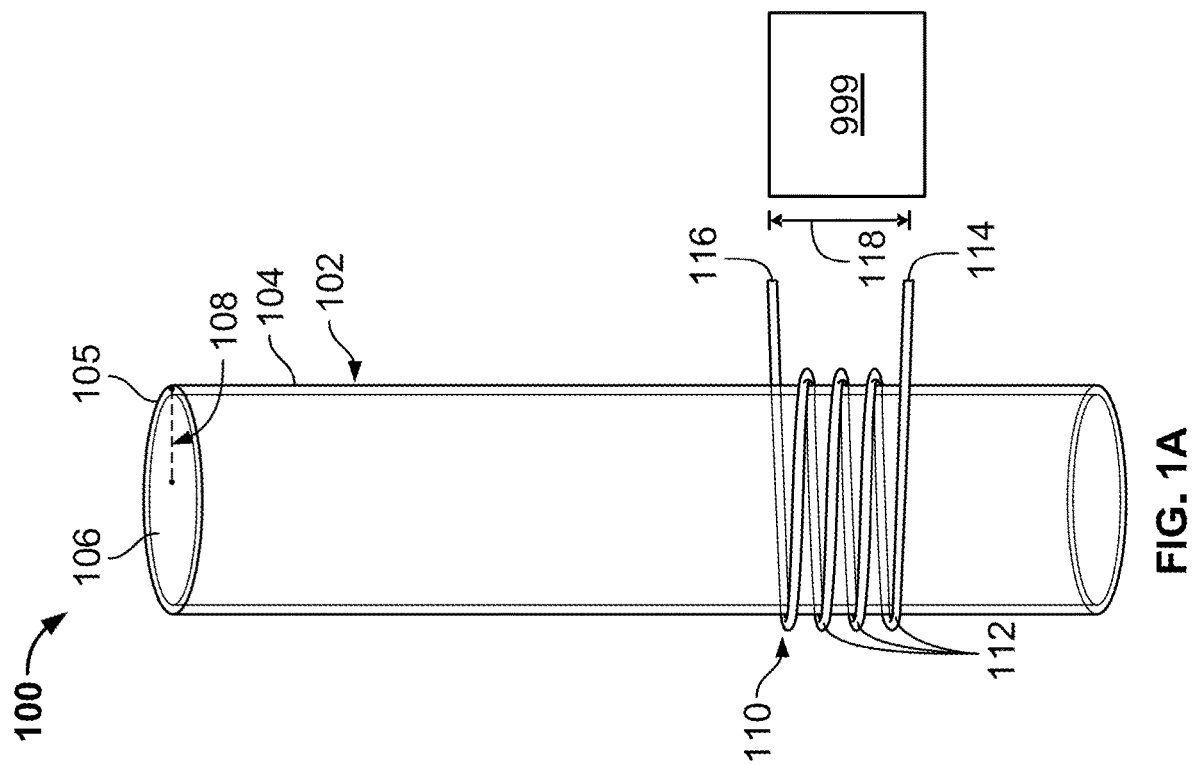
Figure 1C:
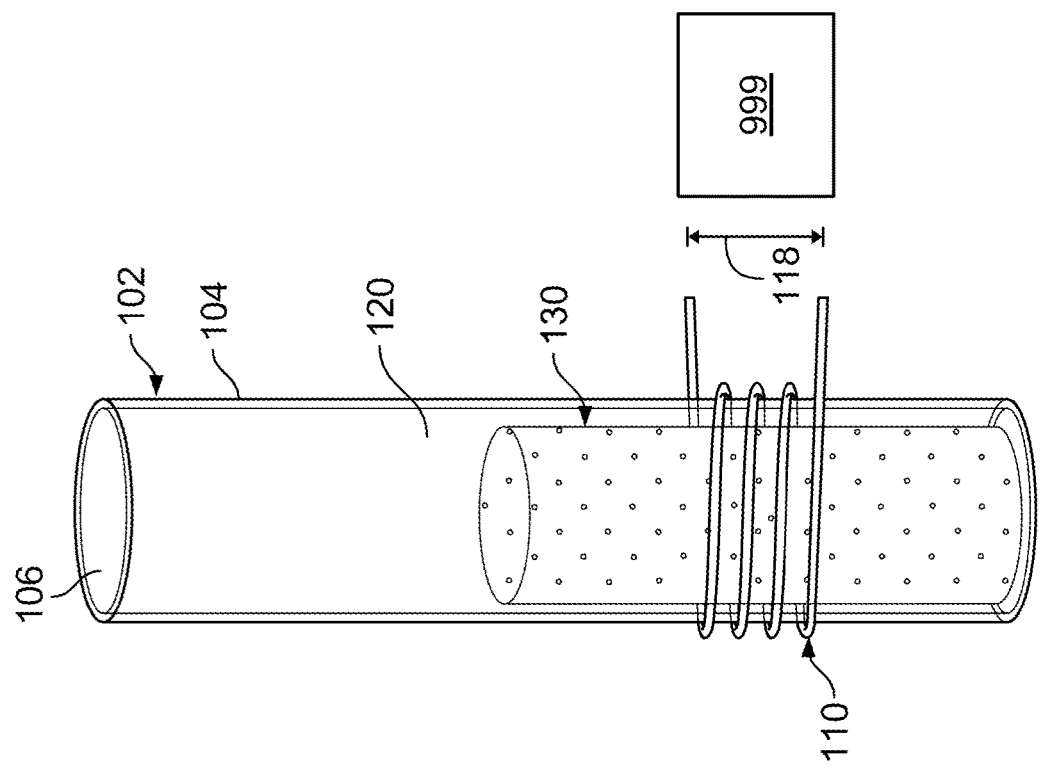
Figure 1D:
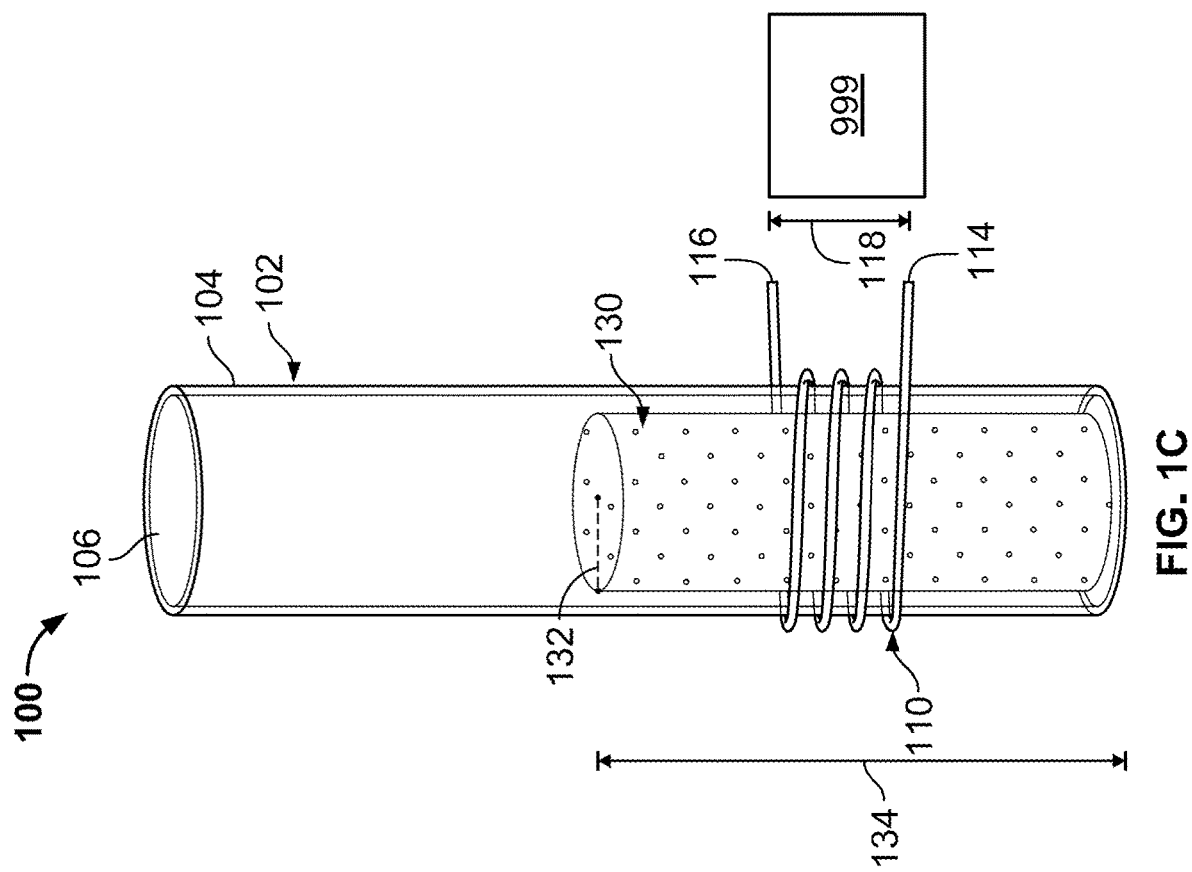

FIGS. 1A-1D are schematic drawings of a rock property measurement system 100 as used in sequential steps in an example method for determining one or more properties of a rock core sample according to the present disclosure. Generally, rock property measurement system 100 can be used according to the example testing method (described with reference to these figures) to measure a fluid uptake capacity in a cylindrically-shaped rock sample 130, otherwise known as a "core sample" that has a substantially circular axial cross-sectional shape and a particular length (as shown in FIGS. 1C-1D). Thus, in rock property measurement system 100 and the example method, the core sample 130 can be tested for fluid uptake properties without crushing the rock sample into powder.

As described in more detail herein, the rock property measurement system 100 can use nuclear magnetic resonance (NMR) measurements to directly measure nuclei in a test fluid within the system 100, thereby directly measuring the fluid uptake. By using core sample 130 rather than crushing a rock sample into particulate or powder, the possibility of added error from an increased surface area of the powder, or any other effects that may occur from physical alteration of the sample, can be reduced or eliminated. Moreover, by using core sample 130 rather than crushing a rock sample into particulate or powder, the core sample 130 can be used for repeated tests and further measurements. In some aspects, the core sample 130 is a type of rock that is non-magnetic and contains less than 10% paramagnetic components (such as pyrite).

In some aspects, the rock property measurement system 100 can be used in the in the measurement of fluid uptake capacity of reservoir rocks, such as unconventional source rocks. In some aspects, the rock property measurement system 100 can be used to measure a carbon dioxide ($CO_2$) storage capacity of a reservoir rock formation under the terranean surface (whether on land or under a body of water). Such measurements can be advantageous as regulatory regimes may require more CO2 sequestration in subterranean formations.

In other aspects, the rock property measurement system 100 can also be used to determine an amount of hydrocarbon (for example, oil, gas, mixed-phase fluid) that can be stored in the core sample 130, and thus a subterranean formation. Such measurements can be used to determine an initial maximum producible hydrocarbon from the core sample and from the subterranean formation.

As shown in FIG. 1A, the rock property measurement system 100 includes a test container 102 that is comprised of a cylinder 104 that defines an inner volume 106 into which a core sample can be inserted (for example, through an open end 105). The cylinder 104 has a particular radius 108 of the inner volume 106 (as well as a length/height) that is sufficient to hold a rock sample of a particular size, such as a core sample of about 3.40 millimeters (mm) in diameter and 40 mm in length. Thus, in this example the cylinder 104 can have a diameter of about 3.58 mm. The aforementioned dimensions, however, are exemplary and other dimensions of the cylinder 104 and a core sample can vary according to other example implementations.

As further shown in FIG. 1A, an NMR coil 110 is positioned around the cylinder 104 (or conversely, the cylinder 104 is positioned within loops 112 of the NMR coil 110. Thus, in this example, the combination of the test container 102 and NMR coil 110 comprises an NMR pressure cell 102. The NMR coil 110 includes contacts 114 and 116 that are separated by a length (or height) 118, which is a distance of a sensitive zone of detection of the NMR coil 110. While the NMR pressure cell 102 in this example includes the cylinder 104, other container shapes (and core sample shapes) can be used without departing from the scope of this disclosure.

The rock property measurement system 100 can be used to implement an example method for determining a fluid uptake in a rock sample. For example, the example method can determine an injected fluid quantity for a core sample (or other regularly shaped porous rock samples in which a bulk volume of the sample can be easily determined from the shape and size) using NMR measurements. Generally, the example method includes subjecting a pressure injection of a test fluid into a rock sample, which can facilitate the determination of the amount of fluid in the sample. To accomplish this, the method includes the collection of multiple NMR spectra that are test fluid-dependent in combination with parameters related to the size of the rock sample and the NMR pressure cell 102.

As shown in FIGS. 1A-1D, an NMR control system 999 is communicably coupled to the NMR coil 110 in order to operate the coil 110 and collect NMR spectra, as well as perform one or more calculations to determine the fluid uptake. In some aspects, the NMR control system 999 comprises a mechanical controller or an electro-mechanical controller. In some aspects, the NMR control system 999 can be a microprocessor-based controller. The NMR control system 999 can be used for the operations described in association with any of the computer-implemented methods described previously. The NMR control system 999, in these aspects, is intended to include various forms of digital computing hardware. Generally, the NMR control system 999 can include one or more processors, one or more memory components, and, in some aspects, an input/output device.

Figure 2:
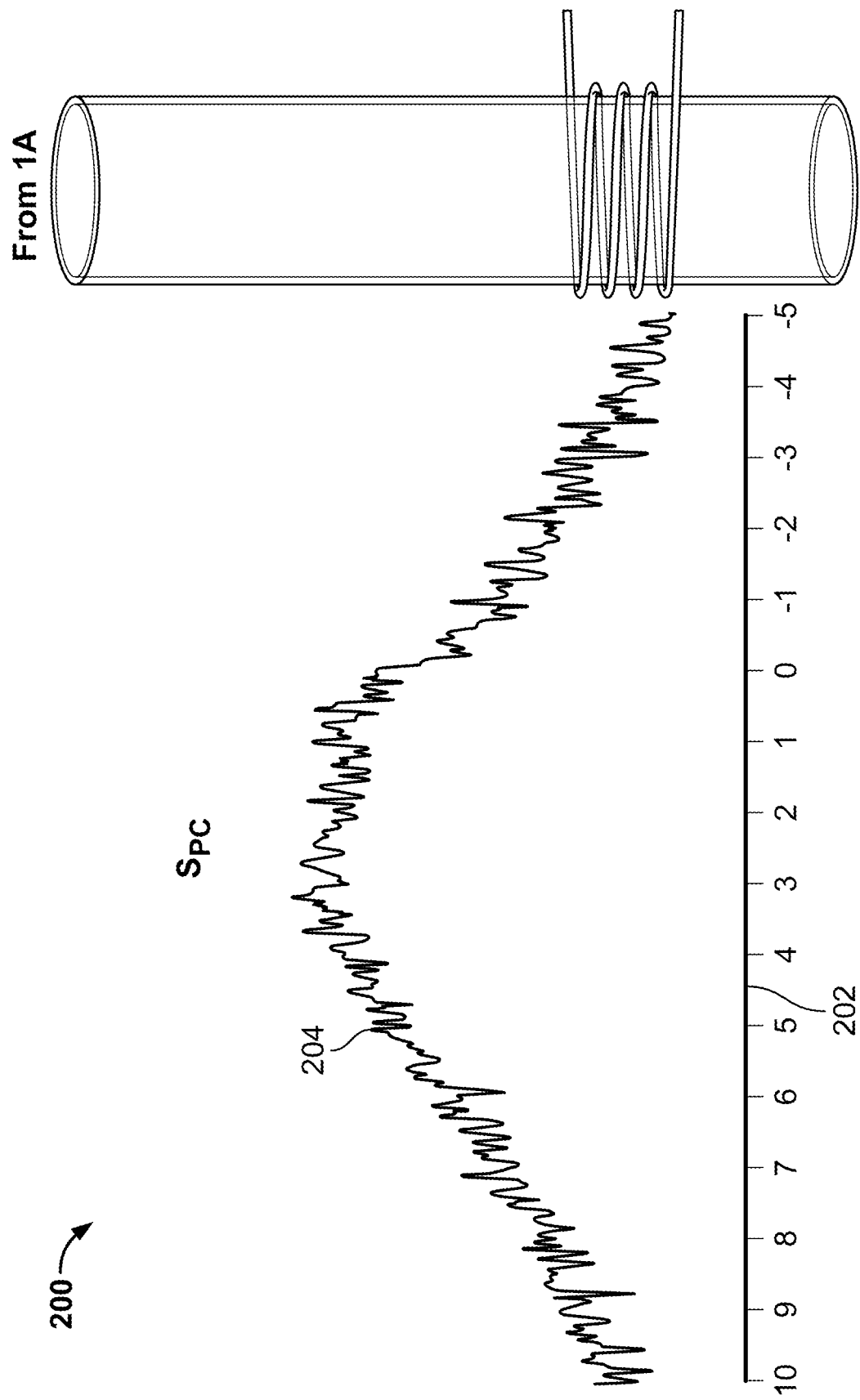
FIGS. 2-7 show graphs of measurements taken during the example method of FIGS. 1A-1D for determining one or more properties of a rock core sample according to the present disclosure.

FIG. 1A shows the rock property measurement system 100 with the cylinder 104 empty, in other words, not holding a rock sample nor holding any test fluid. As part of the example method to determine the rock properties, the rock property measurement system 100 as shown in FIG. 1A is used to determine background NMR spectra. In the example method, using the rock property measurement system 100 shown in FIG. 1A, the empty cylinder 104 is placed in the NMR coil 110 and a vacuum is pulled on the cylinder 104. Next, the NMR coil 110 is operated (for example, by the NMR control system 999) to collect background NMR spectra, $S_{PC}$. Turning briefly to FIG. 2, this figure shows a graph 200 of the collected background NMR spectra, $S_{PC}$, in the step performed in FIG. 1A. Graph 200 includes an x-axis 202 that represents a chemical shift while a y-axis (not shown) represents the volume of fluid in the detection zone of the cylinder 104. A curve 204, as shown, represents the amplitude signal, S, of the background NMR ($S_{PC}$).

Turning now to FIG. 1B, the rock property measurement system 100 is shown prepared for a next step (or steps) of the example method. For example, as shown in FIG. 1B, the cylinder 104 is filled with a test fluid 120. Several test fluids can be used for the test fluid 120. For example, methane (CH4) or CO2 can be used, however, any fluid with an NMR active spin-½ nuclei can be used. Thus, other hydrocarbon fluids (for example, gasses) such as ethane or propane can also be used. Further, nitrogen (for example, N-15 labeled) can be used, with the NMR detection from $^{15}$N rather than $^{13}$C (for carbon dioxide) or $^1$H (for methane or other hydrocarbon).

Figure 3:
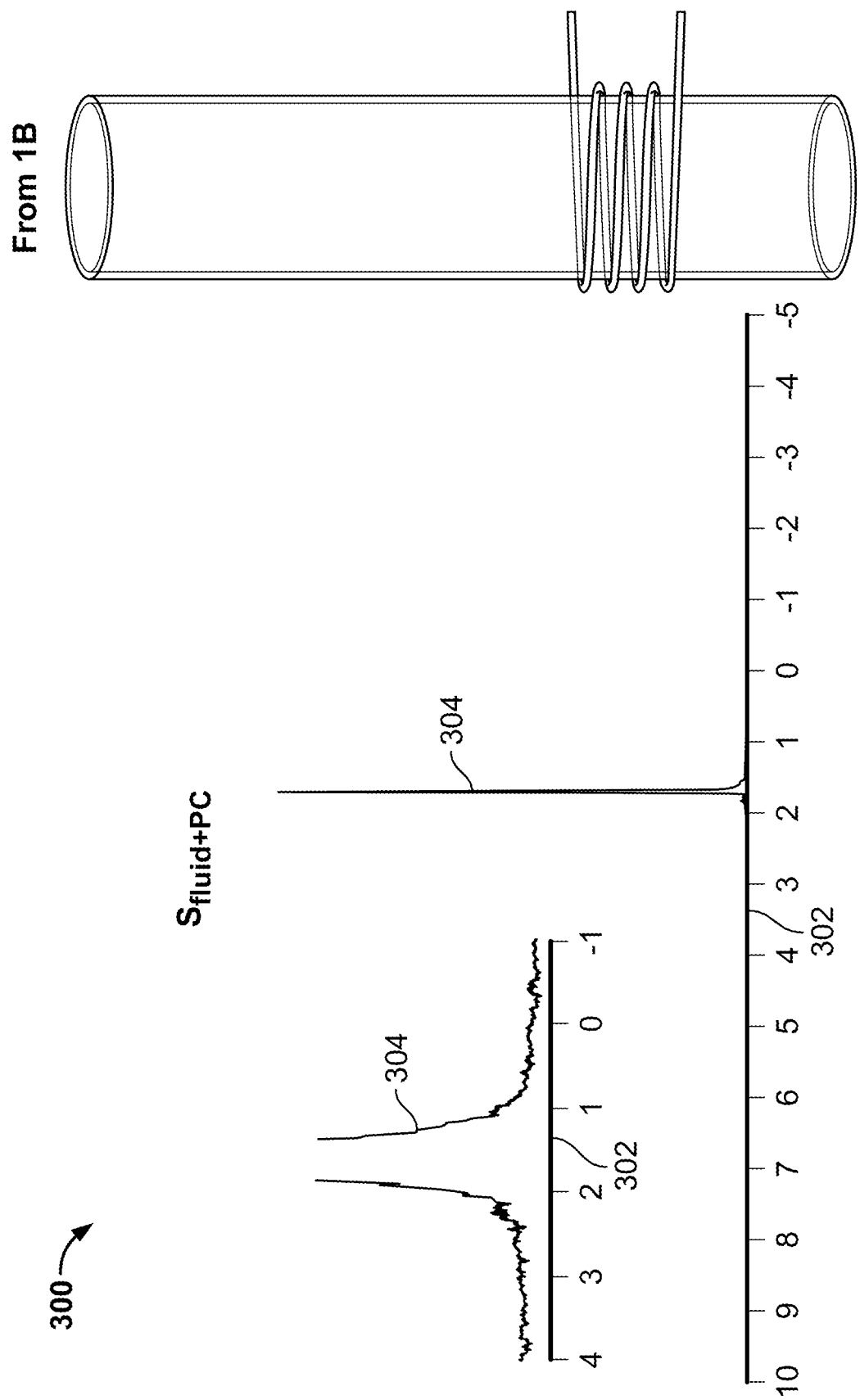

The test fluid 120 can be injected into the empty inner volume 106 at a particular pressure. Once enclosed, the NMR coil 110 is operated (for example, by the NMR control system 999) to collect NMR spectra of the test fluid 120 ($S_{fluid+PC}$). Turning briefly to FIG. 3, this figure shows a graph 300 of the NMR spectra of the test fluid 120, in the step performed in FIG. 1B. Graph 300 includes an x-axis 302 that represents a chemical shift while a y-axis (not shown) represents the volume of fluid in the detection zone of the cylinder 104. A curve 304, as shown, represents the amplitude signal, S, of the NMR spectra of the test fluid 120 ($S_{fluid+PC}$).

Figure 5:
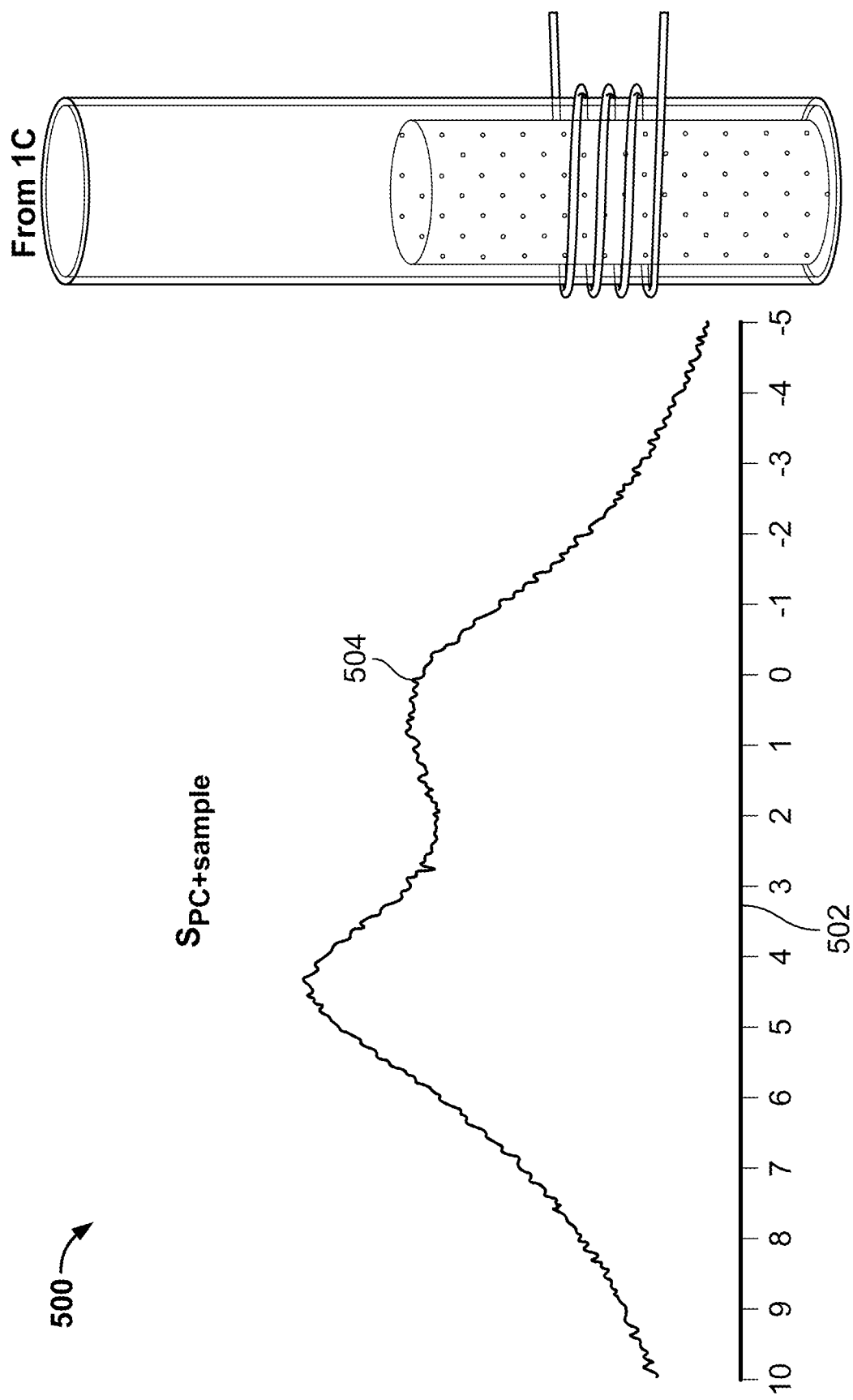

Turning now to FIG. 1C, the rock property measurement system 100 is shown prepared for a next step (or steps) of the example method. For example, as shown in FIG. 1C, the cylinder 104 is emptied of the test fluid 120 and the core sample 130 is inserted into the inner volume 106. A vacuum is pulled on the cylinder 104 with the core sample 130 inserted in the inner volume 106. Next, the NMR coil 110 is operated (for example, by the NMR control system 999) to collect NMR spectra of the core sample 130, $S_{PC+sample}$. Turning briefly to FIG. 5, this figure shows a graph 500 of the collected NMR spectra, $S_{PC+sample}$, in the step performed in FIG. 1C. Graph 500 includes an x-axis 502 that represents a chemical shift while a y-axis (not shown) represents the volume of fluid in the detection zone of the cylinder 104. A curve 504, as shown, represents the amplitude signal, S, of the core sample NMR spectra ($S_{PC+sample}$).

Turning now to FIG. 1D, the rock property measurement system 100 is shown prepared for a next step (or steps) of the example method. For example, as shown in FIG. 1D, the cylinder 104 still holds the core sample 130 in the inner volume 106 and the test fluid 120 is reinserted into the inner volume 106 at the same particular pressure as in FIG. 1B. In some aspects, a particular time delay is implemented after filling the cylinder 104 with the test fluid 120 in order to allow a proper diffusion of the test fluid 120 into the pores of the core sample 130.

In some aspects, an amount of time delay can depend on a type of fluid, a size of the pores, a size of the sample that needs to be imbibed, a pressure, or a combination thereof. For example, assuming a rock with a permeability of 1 mD and a fluid with a diffusion of 2 E−9 m$^2$/s at 1000 psi, then the fluid moves through the sample at approximately 0.1 cm/s. If the sample is 4 cm long, it will take 40 s to travel through the sample. In some aspects, the samples have permeability in the nanodarcy range, which means expected wait times can be anywhere from 5 min to 5 hrs depending on the viscosity (and diffusion) of the fluid. In some aspects, the pressure can be from 75 PSI-15000 psi.

Figure 6:
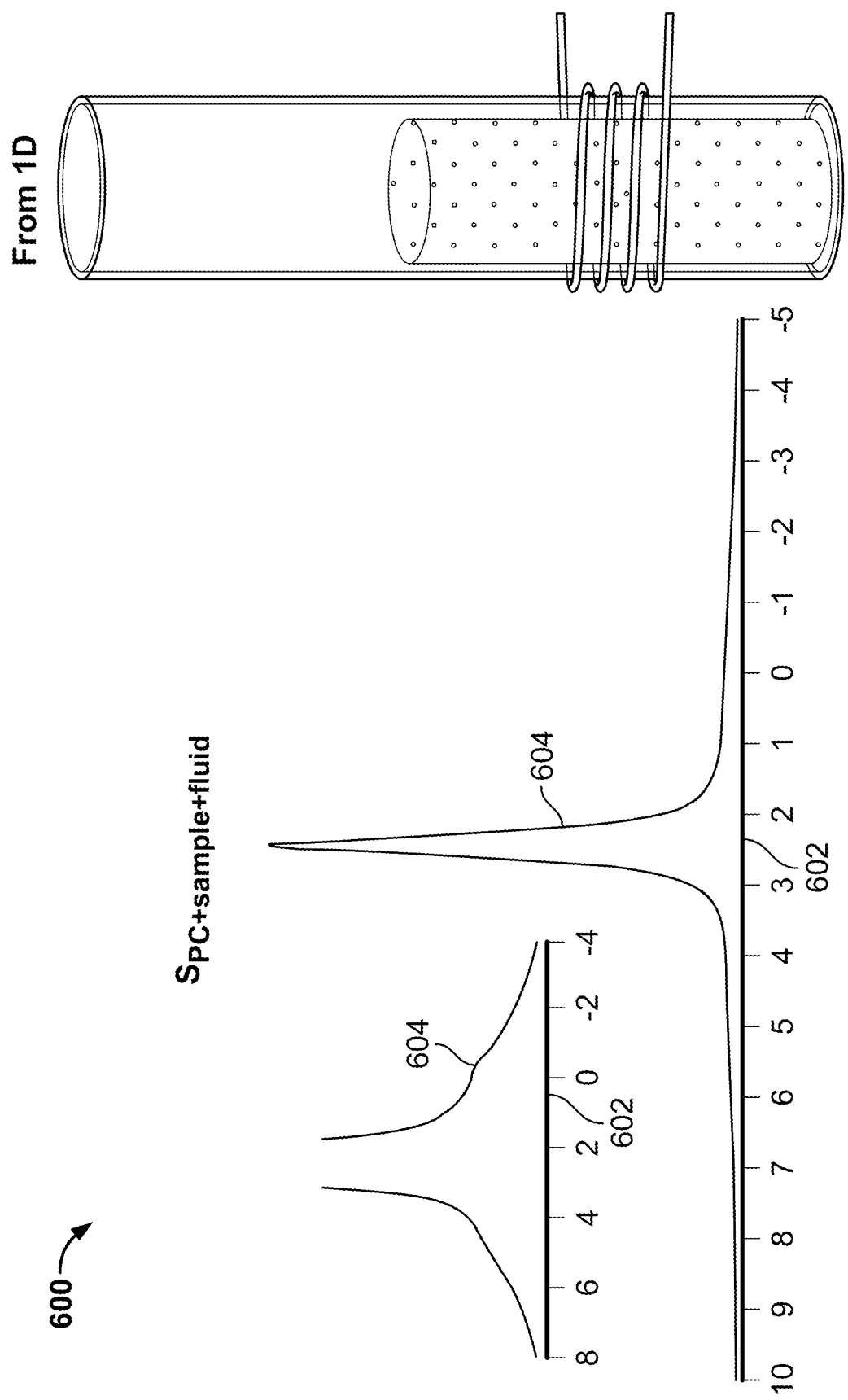

Next, the NMR coil 110 is operated (for example, by the NMR control system 999) to collect NMR spectra of the core sample 130 immersed in the test fluid 120, $S_{PC+sample+fluid}$. Turning briefly to FIG. 6, this figure shows a graph 600 of the collected NMR spectra, $S_{PC+sample+fluid}$, in the step performed in FIG. 1D. Graph 600 includes an x-axis 602 that represents a chemical shift while a y-axis (not shown) represents the volume of fluid in the detection zone of the cylinder 104. A curve 604, as shown, represents the amplitude signal, S, of the core sample NMR spectra in the test fluid ($S_{PC+sample+fluid}$).

Subsequent to the steps of the example test method performed with the rock property measurement system 100, the NMR control system 999 has measured and/or stored the following NMR spectra: $S_{PC}$, $S_{fluid+PC}$, $S_{PC+sample}$, and $S_{PC+sample+fluid}$. Further, other parameters of the rock property measurement system 100 can be known or measured, such as the length (or height) 118 of the sensitive zone of detection in the NMR coil 110, the dimensions (for example, radius 108) of the cylinder 104, as well as the dimensions (for example, radius 132) of the core sample 130. The NMR control system 999 can then perform further steps of the example method to determine the fluid uptake capacity of the core sample 130.

For example, the NMR control system 999 can remove the background spectra in the NMR measurements. In order to determine only the NMR spectra of the test fluid 120 in the NMR pressure cell 102, $S_{PC}$ can be subtracted from $S_{fluid+PC}$:

$$S_{fluid} = S_{fluid+PC} - S_{PC} \quad (1).$$

Figure 4:
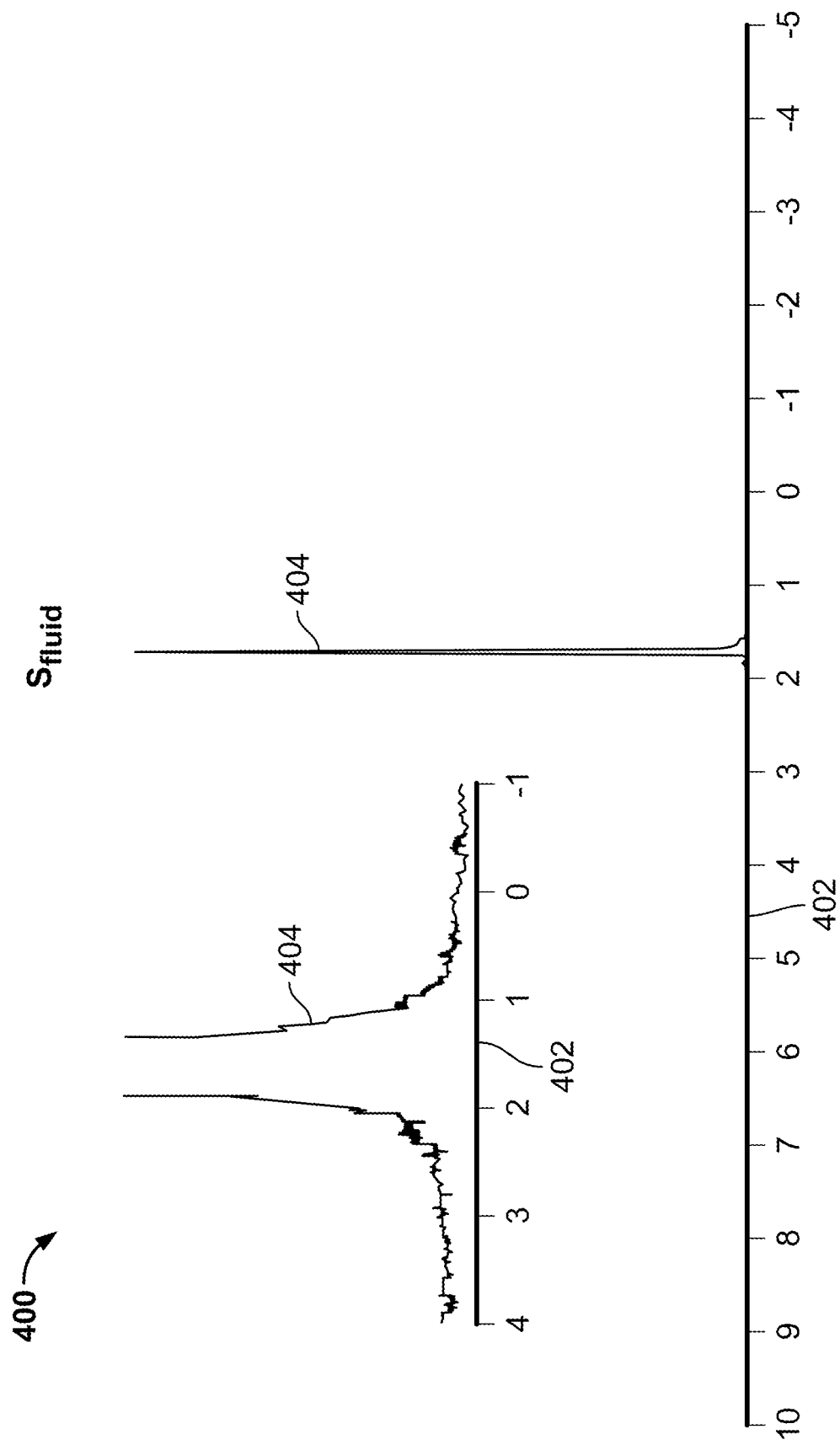

Turning briefly to FIG. 4, this figure shows a graph 400 of the determined NMR spectra, $S_{fluid}$, after the subtraction step performed in Eq. (1). Graph 400 includes an x-axis 402 that represents a chemical shift while a y-axis (not shown) represents an amplitude of fluid in the sensitive region of the coil without the background signal. A curve 404, as shown, represents the amplitude signal, $S_{fluid}$, determined by the amplitude subtraction of $S_{PC}$ from $S_{fluid+PC}$ (each of which were measured by the NMR control system 999).

In order to determine only the NMR spectra of the core sample 130 in the test fluid 120 in the NMR pressure cell 102, $S_{PC+sample}$ can be subtracted from $S_{PC+sample+fluid}$:

$$S_{fluid+sample} = S_{PC+sample+fluid} - S_{PC+sample} \quad (2).$$

Figure 7:
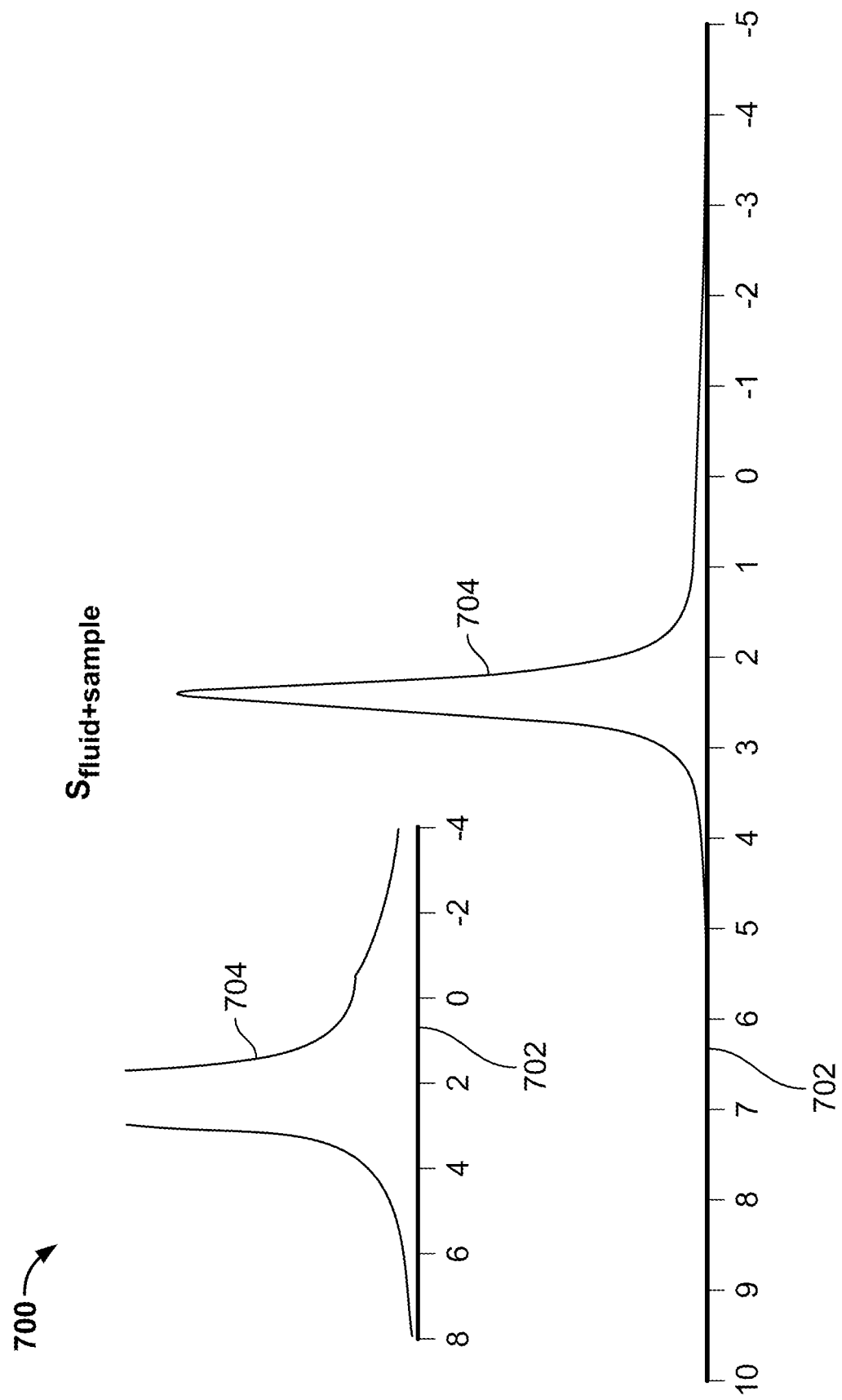

Turning briefly to FIG. 7, this figure shows a graph 700 of the determined NMR spectra, $S_{fluid+sample}$, after the subtraction step performed in Eq. (2). Graph 700 includes an x-axis 702 that represents a chemical shift while a y-axis (not shown) represents an amplitude of fluid in the sensitive region of the coil without the background signal. A curve 704, as shown, represents the amplitude signal, $S_{fluid+sample}$, determined by the amplitude subtraction of $S_{PC+sample}$ from $S_{PC+sample+fluid}$ (each of which were measured by the NMR control system 999).

Once the background spectra in the NMR measurements are removed (for example, by the subtractions shown in Eqs. (1) and (2)), a total uptake volume of the test fluid 120 in the core sample 130 can be calculated by the NMR control system 999. For example, first a total signal of pure bulk test fluid 120 in the NMR pressure cell 102 can be determined based on characteristics of the NMR pressure cell 102:

$$S_{fluid} = \pi r_{PC}^2 h \quad (3).$$

In Eq. 3, $S_{fluid}$ is the total signal of pure bulk test fluid 120 in the NMR pressure cell 102, $r_{PC}$ is the radius 108, and h is the length 118.

Next, the NMR signal of the test fluid 120 with the core sample 130 can be determined:

$$S_{fluid+sample} = (V_{fluid} - V_{sample}) + \phi V_{sample} \quad (4).$$

In Eq. (4), "V" represents a volume, while $\phi$ is the porosity of the core sample 130. In the case of the NMR pressure cell 102 having a cylindrical container (in other words, cylinder 104), Eq. (4) can be rewritten as:

$$S_{fluid+sample} = (\pi r_{PC}^2 - \pi r_{sample}^2)h + \phi \pi r_{sample}^2 h \quad (5).$$

From Eqs. (3), (4), and (5), the following equation can be developed:

$$\phi = \frac{S_{fluid+sample} r_{PC}^2}{S_{fluid} r_{sample}^2} - \frac{r_{PC}^2}{r_{sample}^2} + 1. \quad (6)$$

The total amount of the test fluid 120 in the core sample 130, therefore, is:

$$V_{fluidinsample} = \phi \pi r_{sample}^2 l \quad (7).$$

In Eq. (7), l is the length 134 of the core sample 130.

In an example test performed with the illustrated rock property measurement system 100, a cylindrical plug (core sample 130) was used with methane being the test fluid 120. In the example test, the core sample 130 had a diameter of 3.40 mm (with radius 132 of 1.7 mm) and a length (length 134) of 40 mm. The cylinder 104 has an internal diameter of 3.58 mm (radius 108 of 1.79 mm). For this test core sample 130, first, a vacuum was pulled on the empty cylinder 104 (without the methane or the core sample) and the background NMR spectra signal was collected by the NMR control system 999. This background NMR spectra signal was recorded as curve 204 in FIG. 2 (as $S_{PC}$). Next, methane gas was injected into the cylinder 104 at a particular pressure of 1000 psi. The NMR spectra of the methane in the cylinder 104 (without the core sample) was recorded as curve 304 in FIG. 3 (as $S_{fluid+PC}$). The bulk volume of methane in the NMR pressure cell 102 was then determined as the methane NMR spectrum signal was subtracted by the background spectrum NMR signal. The result of this subtraction is shown as curve 404 in FIG. 4 (as $S_{fluid}$); curve 404 thus represents a signal from pure bulk methane in the NMR pressure cell 102. The quantity of methane is the integration of the spectrum signal (in other words, area under curve 404). For this sample the quantity was calculated to be $2.62 \times 10^7$ mu (machine units).

Continuing the example test, next, the core sample 130 was placed in the cylinder 104 and a vacuum was pulled. The NMR signal was again acquired by the NMR control system 999, with that signal represented by curve 504 in FIG. 5. This is the background signal including contribution from the sample, the pressure cell and the probe and is $S_{PC+sample}$.

Next, the NMR pressure cell 102 was injected with methane gas at the same pressure, 1000 PSI, and an NMR signal was again acquired after injection. The acquired signal is represented by curve 604 in FIG. 6 (as $S_{PC+sample+fluid}$). This spectrum contains the methane signal from the pores inside the core sample, bulk space between the core sample and inner wall of cylinder 104, and the background signal. The background signal was then subtracted. The remaining signal is thus the injected methane in both bulk and core sample pore space (as $S_{fluid+sample}$). This quantity was calculated as $1.06 \times 10^8$ mu.

Next, with this calculated quantity, as well as the radius 132, the radius 108, and the measured NMR signals, Eq. (6) can be used to calculate the porosity ($\phi$) of the core sample 130. Next, using the calculated porosity and dimensions of the core sample 130, the fluid uptake volume ($V_{fluidinsample}$) can be calculated with Eq. (7). Here, the calculated value is 4.4 pu (porosity units).

Figure 8:
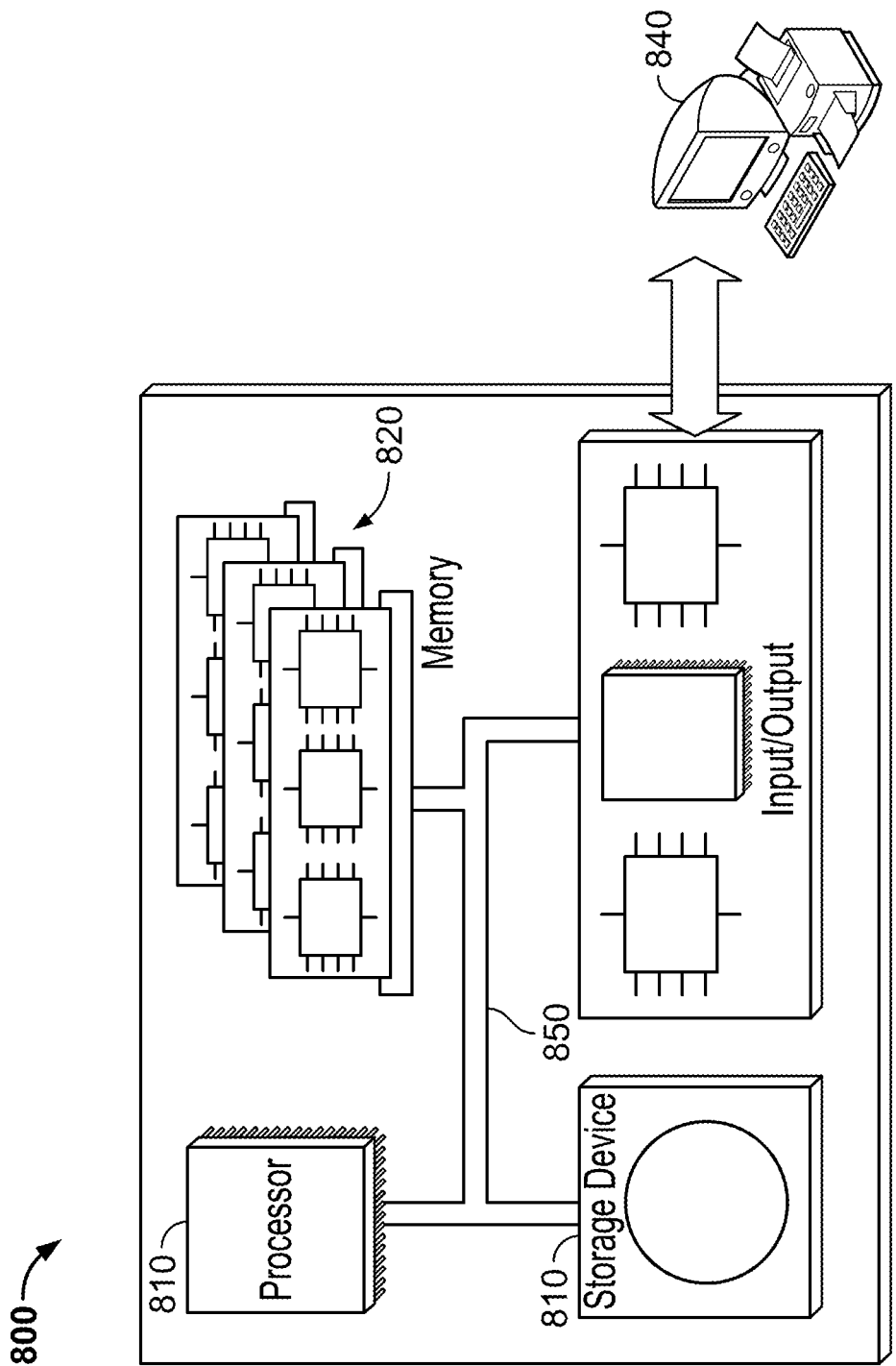
FIG. 8 shows a schematic drawing of a control system that can be used in the example method of FIGS. 1A-1D for determining one or more properties of a rock core sample according to the present disclosure.

FIG. 8 is a schematic illustration of an example control system 800 for a rock property measurement system according to the present disclosure. For example, all or parts of the control system (or controller) 800 can be used for the operations described previously, for example as or as part of the NMR control system 999. The controller 800 is intended to include various forms of digital computers, such as printed circuit boards (PCB), processors, digital circuitry, or otherwise. Additionally, the system can include portable storage media, such as, Universal Serial Bus (USB) flash drives. For example, the USB flash drives may store operating systems and other applications. The USB flash drives can include input/output components, such as a wireless transmitter or USB connector that may be inserted into a USB port of another computing device.

The controller 800 includes a processor 810, a memory 820, a storage device 830, and an input/output device 840. Each of the components 810, 820, 830, and 840 are interconnected using a system bus 850. The processor 810 is capable of processing instructions for execution within the controller 800. The processor may be designed using any of a number of architectures. For example, the processor 810 may be a CISC (Complex Instruction Set Computers) processor, a RISC (Reduced Instruction Set Computer) processor, or a MISC (Minimal Instruction Set Computer) processor.

In one implementation, the processor 810 is a single-threaded processor. In another implementation, the processor 810 is a multi-threaded processor. The processor 810 is capable of processing instructions stored in the memory 820 or on the storage device 830 to display graphical information for a user interface on the input/output device 840.

The memory 820 stores information within the control system 800. In one implementation, the memory 820 is a computer-readable medium. In one implementation, the memory 820 is a volatile memory unit. In another implementation, the memory 820 is a non-volatile memory unit.

The storage device 830 is capable of providing mass storage for the controller 800. In one implementation, the storage device 830 is a computer-readable medium. In various different implementations, the storage device 830 may be a floppy disk device, a hard disk device, an optical disk device, a tape device, flash memory, a solid state device (SSD), or a combination thereof.

The input/output device 840 provides input/output operations for the controller 800. In one implementation, the input/output device 840 includes a keyboard and/or pointing device. In another implementation, the input/output device 840 includes a display unit for displaying graphical user interfaces.

The features described can be implemented in digital electronic circuitry, or in computer hardware, firmware, software, or in combinations of them. The apparatus can be implemented in a computer program product tangibly embodied in an information carrier, for example, in a machine-readable storage device for execution by a programmable processor; and method steps can be performed by a programmable processor executing a program of instructions to perform functions of the described implementations by operating on input data and generating output. The described features can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, solid state drives (SSDs), and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the features can be implemented on a computer having a display device such as a CRT (cathode ray tube) or LCD (liquid crystal display) or LED (light-emitting diode) monitor for displaying information to the user and a keyboard and a pointing device such as a mouse or a trackball by which the user can provide input to the computer. Additionally, such activities can be implemented via touchscreen flat-panel displays and other appropriate mechanisms.

The features can be implemented in a control system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of digital data communication such as a communication network. Examples of communication networks include a local area network ("LAN"), a wide area network ("WAN"), peer-to-peer networks (having ad-hoc or static members), grid computing infrastructures, and the Internet.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

A number of implementations have been described. Nevertheless, it will be understood that various modifications may be made without departing from the spirit and scope of the disclosure. For example, example operations, methods, or processes described herein may include more steps or fewer steps than those described. Further, the steps in such example operations, methods, or processes may be performed in different successions than that described or illustrated in the figures. Accordingly, other implementations are within the scope of the following claims.

What is claimed is:

1. A method for determining at least one rock property of a core sample, comprising:
    measuring a first nuclear magnetic resonance (NMR) spectrum signal of a test fluid enclosed at a particular pressure in a cylinder of an NMR pressure cell;
    measuring a second NMR spectrum signal of a core sample immersed in the test fluid that is enclosed at the particular pressure in the cylinder of the NMR pressure cell;
    removing a background NMR spectrum signal from the first and second NMR spectrum signals to determine a bulk test fluid NMR spectrum signal and a combined test fluid and core sample NMR spectrum signal;
    determining a porosity of the core sample based on the bulk test fluid NMR spectrum signal, the combined test fluid and core sample NMR spectrum signal, at least one dimension of the core sample, and at least one dimension of the cylinder; and
    determining a fluid intake capacity of the core sample based at least in part on the porosity and the at least one dimension of the core sample.

2. The method of claim 1, wherein removing the background NMR spectrum signal from the first and second NMR spectrum signals comprises:
    removing a first background NMR spectrum signal from the first NMR spectrum signal; and
    removing a second background NMR spectrum signal from the second NMR spectrum signal.

3. The method of claim 2, further comprising:
    measuring the first background NMR spectrum signal of the cylinder at a vacuum and independent of the test fluid and the rock sample; and
    measuring the second background NMR spectrum signal of the cylinder with the rock sample at a vacuum and independent of the test fluid.

4. The method of claim 2, wherein removing the first background NMR spectrum signal from the first NMR spectrum signal comprises subtracting an amplitude of the first background NMR spectrum signal from an amplitude of the first NMR spectrum signal across a chemical shift; and
    removing the second background NMR spectrum signal from the second NMR spectrum signal comprises subtracting an amplitude of the second background NMR spectrum signal from an amplitude of the second NMR spectrum signal across the chemical shift.

5. The method of claim 1, wherein the at least one dimension of the core sample comprises a cross-sectional radius or diameter of the core sample, and the at least one dimension of the cylinder comprises a cross-sectional radius or diameter of an inner volume of the cylinder.

6. The method of claim 5, wherein determining the fluid intake capacity of the core sample based at least in part on the porosity and the at least one dimension of the core sample comprises:
  determining the fluid intake capacity of the core sample based on the porosity, the cross-sectional radius or diameter of the core sample, and a length of the core sample.

7. The method of claim 6, wherein the core sample is cylindrical.

8. The method of claim 1, wherein the test fluid comprises methane, and the NMR spectrum signal comprises a $^1$H or a $^{13}$C signal.

9. The method of claim 1, wherein the test fluid comprises carbon dioxide, and the NMR spectrum signal comprises a $^{13}$C signal.

10. A system for determining at least one rock property of a core sample, comprising:
  a nuclear magnetic resonance (NMR) pressure cell, comprising:
    a test cylinder configured to hold a test fluid and a core sample; and
    an NMR coil positioned around the test cylinder and configured to measure NMR spectrum signals of the test cylinder;
  a control system communicably coupled to the NMR coil and configured to perform operations comprising:
    measuring a first nuclear magnetic resonance (NMR) spectrum signal of the test fluid enclosed at a particular pressure in the test cylinder;
    measuring a second NMR spectrum signal of the core sample immersed in the test fluid that is enclosed at the particular pressure in the test cylinder;
    removing a background NMR spectrum signal from the first and second NMR spectrum signals to determine a bulk test fluid NMR spectrum signal and a combined test fluid and core sample NMR spectrum signal;
    determining a porosity of the core sample based on the bulk test fluid NMR spectrum signal, the combined test fluid and core sample NMR spectrum signal, at least one dimension of the core sample, and at least one dimension of the test cylinder; and
    determining a fluid intake capacity of the core sample based at least in part on the porosity and the at least one dimension of the core sample.

11. The system of claim 10, wherein the operation of removing the background NMR spectrum signal from the first and second NMR spectrum signals comprises:
  removing a first background NMR spectrum signal from the first NMR spectrum signal; and
  removing a second background NMR spectrum signal from the second NMR spectrum signal.

12. The system of claim 11, wherein the control system is configured to perform operations comprising:
  measuring the first background NMR spectrum signal of the cylinder at a vacuum and independent of the test fluid and the rock sample; and
  measuring the second background NMR spectrum signal of the cylinder with the rock sample at a vacuum and independent of the test fluid.

13. The system of claim 11, wherein the operation of removing the first background NMR spectrum signal from the first NMR spectrum signal comprises subtracting an amplitude of the first background NMR spectrum signal from an amplitude of the first NMR spectrum signal across a chemical shift; and
  the operation of removing the second background NMR spectrum signal from the second NMR spectrum signal comprises subtracting an amplitude of the second background NMR spectrum signal from an amplitude of the second NMR spectrum signal across the chemical shift.

14. The system of claim 10, wherein the at least one dimension of the core sample comprises a cross-sectional radius or diameter of the core sample, and the at least one dimension of the cylinder comprises a cross-sectional radius or diameter of an inner volume of the cylinder.

15. The system of claim 14, wherein the operation of determining the fluid intake capacity of the core sample based at least in part on the porosity and the at least one dimension of the core sample comprises:
  determining the fluid intake capacity of the core sample based on the porosity, the cross-sectional radius or diameter of the core sample, and a length of the core sample.

16. The system of claim 15, wherein the core sample is cylindrical.

17. The system of claim 10, wherein the test fluid comprises methane, and the NMR spectrum signal comprises a $^1$H or a $^{13}$C signal.

18. The system of claim 10, wherein the test fluid comprises carbon dioxide, and the NMR spectrum signal comprises a $^{13}$C signal.

19. A computer-implemented method for determining at least one rock property of a core sample, comprising:
  identifying, with at least one hardware processor, measurements of a first nuclear magnetic resonance (NMR) spectrum signal of a test fluid enclosed at a particular pressure in a cylinder of an NMR pressure cell;
  identifying, with the at least one hardware processor, measurements of a second NMR spectrum signal of a core sample immersed in the test fluid that is enclosed at the particular pressure in the cylinder of the NMR pressure cell;
  removing, with the at least one hardware processor, a background NMR spectrum signal from the first and second NMR spectrum signals to determine a bulk test fluid NMR spectrum signal and a combined test fluid and core sample NMR spectrum signal;
  determining, with the at least one hardware processor, a porosity of the core sample based on the bulk test fluid NMR spectrum signal, the combined test fluid and core sample NMR spectrum signal, at least one dimension of the core sample, and at least one dimension of the cylinder; and
  determining, with the at least one hardware processor, a fluid intake capacity of the core sample based at least in part on the porosity and the at least one dimension of the core sample.

20. The computer-implemented method of claim 19, wherein removing the background NMR spectrum signal from the first and second NMR spectrum signals comprises:
  removing, with the at least one hardware processor, a first background NMR spectrum signal from the first NMR spectrum signal; and removing, with the at least one hardware processor, a second background NMR spectrum signal from the second NMR spectrum signal.

21. The computer-implemented method of claim 20, further comprising:

identifying, with the at least one hardware processor, measurements of the first background NMR spectrum signal of the cylinder at a vacuum and independent of the test fluid and the rock sample; and identifying, with the at least one hardware processor, measurements of the second background NMR spectrum signal of the cylinder with the rock sample at a vacuum and independent of the test fluid.

22. The computer-implemented method of claim 20, wherein removing the first background NMR spectrum signal from the first NMR spectrum signal comprises subtracting, with the at least one hardware processor, an amplitude of the first background NMR spectrum signal from an amplitude of the first NMR spectrum signal across a chemical shift; and removing the second background NMR spectrum signal from the second NMR spectrum signal comprises subtracting, with the at least one hardware processor, an amplitude of the second background NMR spectrum signal from an amplitude of the second NMR spectrum signal across the chemical shift.

23. The computer-implemented method of claim 19, wherein the at least one dimension of the core sample comprises a cross-sectional radius or diameter of the core sample, and the at least one dimension of the cylinder comprises a cross-sectional radius or diameter of an inner volume of the cylinder.

24. The computer-implemented method of claim 23, wherein determining the fluid intake capacity of the core sample based at least in part on the porosity and the at least one dimension of the core sample comprises:

determining, with the at least one hardware processor, the fluid intake capacity of the core sample based on the porosity, the cross-sectional radius or diameter of the core sample, and a length of the core sample.

25. The computer-implemented method of claim 19, wherein the test fluid comprises methane, and the NMR spectrum signal comprises a $^1H$ or a $^{13}C$ signal.

26. The computer-implemented method of claim 19, wherein the test fluid comprises carbon dioxide, and the NMR spectrum signal comprises a $^{13}C$ signal.

* * * * *